United States Patent [19]

Bower

[11] 4,159,718

[45] Jul. 3, 1979

[54] DISPOSABLE DOUCHE

[76] Inventor: Earle S. Bower, 633 Third Ave., New York, N.Y. 10017

[21] Appl. No.: 817,049

[22] Filed: Jul. 19, 1977

[51] Int. Cl.² ............................................. A61M 7/00
[52] U.S. Cl. ..................................... 128/248; 128/251
[58] Field of Search .............. 128/248, 251, 232, 231, 128/233, 239, 247; 229/3.1; 222/107

[56] References Cited

U.S. PATENT DOCUMENTS

| 2,568,915 | 9/1951 | Friedman | 128/251 |
| 2,661,741 | 12/1953 | Puckman | 128/232 |
| 3,144,866 | 8/1964 | Elles | 128/232 |
| 3,371,665 | 3/1968 | Druckenmiller et al. | 128/239 |
| 3,530,858 | 9/1970 | Edwards | 128/232 |
| 3,559,872 | 2/1971 | Riboud | 229/3.1 |
| 3,844,284 | 10/1974 | Schornfeld et al. | 128/232 |

*Primary Examiner*—Lawrence W. Trapp
*Attorney, Agent, or Firm*—Pennie & Edmonds

[57] ABSTRACT

A disposable douche made up of two sheets of a thin plastic material sealed together along their edges to form a bag having a closed end. A treated paper tubular joiner section extends into the bag opposite the closed end with the sheets being sealed to the joiner section along a portion of its length. A treated paper tubular probe section is adapted to slidably and sealingly engage the interior of the joiner section. The bag may be filled with a liquid when the probe is removed from the joiner section.

7 Claims, 3 Drawing Figures

DISPOSABLE DOUCHE

DESCRIPTION OF THE PRIOR ART

Disposable douches have been proposed which incorporate relatively expensive molded plastic parts which increase the cost of the item. For example see the disposable douche disclosed in U.S. Pat. No. 3,144,866. It is an object of my invention to provide for a disposable douche which will incorporate a minimum of easily formed parts where the parts are formed of inexpensive materials such as paper and thin plastic sheeting.

Prior art disposable douches of which I am aware are of relatively small volume, on the order of 6 liquid ounces, whereas the user often desires a greater amount on the order of 12–16 liquid ounces. A problem associated with use of large volume douches is that the packages in which the douches are sold are necessarily large. It is therefore a further object of my invention to provide for a disposable douche which may be packaged for sale to a consumer in an unfilled state such that it may be packaged in a small unobtrusive manner. The douche bag when sold may contain a medicinal product and the bag is designed to be easily filled by the consumer with a liquid prior to use.

GENERAL DESCRIPTION OF THE INVENTION

A disposable douche according to the invention broadly comprises two sheets of a thin plastic material which are sealed together along a major portion of their peripheries to form a bag having a closed end. A treated paper tubular section extends into a filler end of the bag opposite the sealed end and has the plastic sheeting sealed onto a portion of the length of the tubular section. A separate treated paper tubular probe section is adapted to sealingly and slidably engage the interior of the joiner section when the disposable douche is assembled for use. The bag is adapted to be filled with a liquid through the joiner section after which the probe is inserted.

Preferably the joiner section is precoated with a thin plastic material which is the same as the plastic material comprising the sheets in order to facilitate sealing of the sheets onto the exterior of the joiner section.

DETAILED DESCRIPTION OF THE PREFERRED EMBODIMENT

Figure 1:
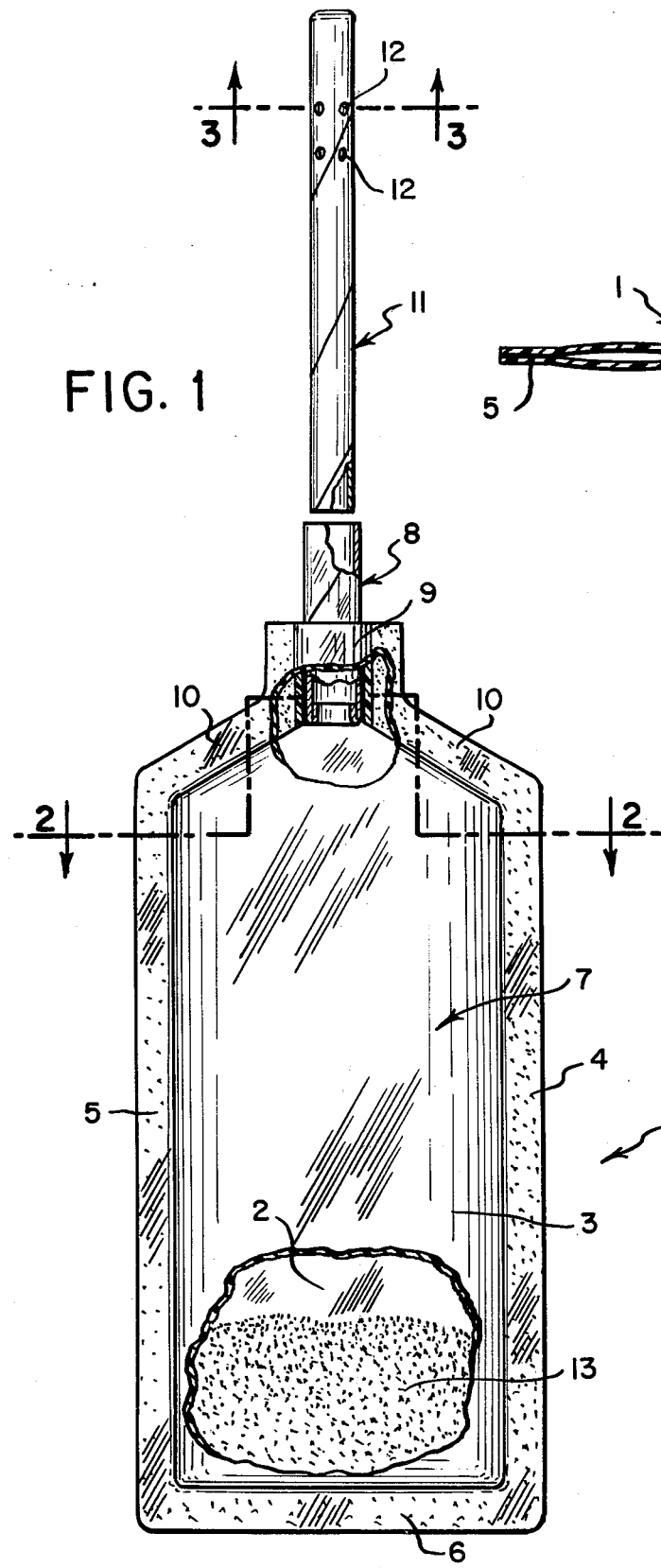
FIG. 1 is a broken plan view of a disposable douche constructed according to the invention.
Figure 2:
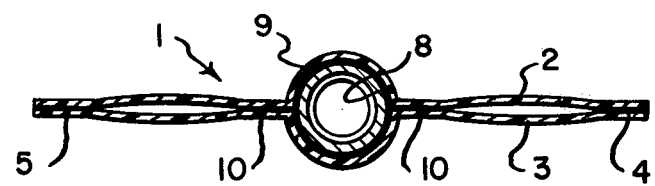
FIG. 2 is a sectional view of FIG. 1 taken along lines 2—2.
Figure 3:
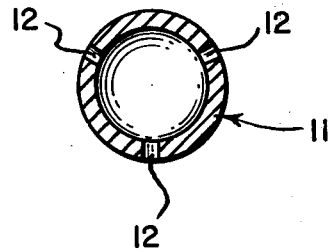
FIG. 3 is an enlarged sectional view of FIG. 1 taken along lines 3—3.

Referring to the drawings and in particular to FIG. 1, there is disclosed a disposable douche 1 comprising two rectangular sheets 2 and 3 which are heat sealed together along their long edges 4 and 5 as well as at the short edge end 6 to form a bag 7 having a closed end. A joiner section 8 comprising a spiral wound treated paper tube is inserted into the bag 7. The sheets 2 and 3 are sealed to the joiner section 8 along a portion of its length 9 as well as to each other along seams 10 in order to form the filler end of the bag 7.

A probe 11 comprising a spiral wound treated paper tubular section is adapted to slidably and sealingly engage the interior of the joiner section 8. The probe section has orifices 12 positioned near the outer end thereof. Preferably there are two rows each having three orifices 12 positioned circumferentially 120° apart. The rows are positioned about $\frac{3}{4}''$ and $1''$ respectively from the end of the probe.

The bag 7 may contain a medicinal product 13 which is adapted to mix with liquid when the bag 7 is filled by the user through the joiner section 8. The douche when sold may have the probe 11 positioned in the joiner section to keep the powder within the bag. In this event the probe 11 is moved from the joiner section prior to filling. After the bag is filled the probe 11 is inserted into the joiner section after which the disposable douche 1 is ready for use.

Preferably the sheets 2 and 3 each comprise a 50 gauge polyester material adhesively laminated to a low density polyethylene material of approximately $1\frac{1}{2}$ mils thickness.

The joiner section 8 is a spiral wound hollow white sulfite paper tube coated with a 1 mil polyethylene coating on the outside surface to facilitate the joining with the polyethylene material comprising the sheets 2 and 3.

The probe section 11 is a spiral wound tube flat rolled at one end and sealed with an approved adhesive. The tube itself may comprise two layers of a white sulfite paper, one layer of a white kraft paper and one layer of a white flint paper.

The joiner section 8 is heat sealed to the plastic sheets by utilizing a contoured die which is formed around and heat sealed to the joiner section. A locating pin positions the joiner tube to the contoured die after which the die parts are closed to heat seal the sheets to the joiner section. The die parts are then opened to release the complete bag 7.

It is seen that a disposable douche constructed according to the invention has a minimum of parts, utilizes inexpensively formed parts made of inexpensive materials and at the same time provides an assembly which will be of a minimum size for convenient packaging.

While I have described the structure of a disposable douche, it is apparent that it could also have application as a large volume enema for hosipital use. In this event the probe structure would be modified slightly to provide a soft molded plastic tip and a compatible joiner tube.

I claim:

1. A disposable douche comprising two sheets of a thin plastic material sealed together along a major portion of their edges to form a bag having a closed end, a tubular joiner section extending into an end of the bag opposite said closed end with said sheets being heat sealed to the outer surface of said joiner section along a portion of its length to form a permanent seal and to each other to form a filler end of the bag, and an axially slidable tubular probe section sealingly engaging the interior of said tubular joiner section whereby when said probe is axially slid from said joiner section the bag may be filled with a liquid through said joiner section and whereby when said probe is axially slid into said joiner section said douche is ready for use.

2. A disposable douche according to claim 1 wherein said tubular joiner section and said tubular probe section each comprise a treated paper.

3. A disposable douche according to claim 2 wherein said joiner section and said probe section each comprise a spiral wound tube.

4. A disposable douche according to claim 2 wherein the exterior of the paper joiner section is coated with a thin coating of the same plastic material comprising the sheets to facilitate sealing of the sheets to the joiner section.

5. A disposable douche according to claim 2 wherein the interior surface of the tubular probe has thin wax film impregnated thereon.

6. A disposable douche according to claim 1 wherein said sheets are substantially rectangular in shape with the closed end and filling end of said bag being formed by the short edges of the sheets.

7. A disposable douche comprising two substantially rectangular sheets of a thin plastic material sealed together along their long edges and along one of their short edges to form a substantially rectangular shaped bag having a closed end, a treated paper spiral wound tubular joiner section having a thin plastic coating on the exterior thereof of the same plastic material comprising the sheets with said joiner section extending into the end of the bag opposite said closed end and with said sheets being heat sealed to the outer surface of said joiner section along a portion of its length and to each other to form a filler end of the bag, and an axially slidable treated paper spiral wound tubular probe section having a thin coating of wax impregnated on the interior surface thereof sealingly engaging the interior of said tubular section and adapted to be moved axially with respect to said tubular section.

* * * * *